United States Patent
Elgart

(10) Patent No.: US 11,712,032 B2
(45) Date of Patent: Aug. 1, 2023

(54) DEVICE TO DETECT AND EXERCISE CONTROL OVER WEEDS APPLIED ON AGRICULTURAL MACHINERY

(71) Applicant: Milar Agro Tech S.r.l., Buenos Aires (AR)

(72) Inventor: Leonardo Elgart, Buenos Aires (AR)

(73) Assignee: Milar Agro Tech S.r.l., Pcia. de Buenos Aires (AR)

( * ) Notice: Subject to any disclaimer, the term of this patent is extended or adjusted under 35 U.S.C. 154(b) by 522 days.

(21) Appl. No.: 16/818,209

(22) Filed: Mar. 13, 2020

(65) Prior Publication Data

US 2020/0375172 A1 Dec. 3, 2020

(51) Int. Cl.

| | |
|---|---|
| *A01M 7/00* | (2006.01) |
| *B05B 1/20* | (2006.01) |
| *B05B 1/16* | (2006.01) |
| *B05B 12/12* | (2006.01) |
| *G06V 20/10* | (2022.01) |
| *G01N 33/00* | (2006.01) |
| *G06T 7/00* | (2017.01) |
| *G06T 7/507* | (2017.01) |
| *G06T 7/62* | (2017.01) |
| *G06T 7/90* | (2017.01) |
| *G06V 20/68* | (2022.01) |

(52) U.S. Cl.
CPC ........ *A01M 7/0089* (2013.01); *A01M 7/0042* (2013.01); *B05B 1/169* (2013.01); *B05B 1/20* (2013.01); *B05B 12/122* (2013.01); *G01N 33/0098* (2013.01); *G06T 7/0006* (2013.01); *G06T 7/507* (2017.01); *G06T 7/62* (2017.01); *G06T 7/90* (2017.01); *G06V 20/188* (2022.01); *G06T 2207/30188* (2013.01); *G06V 20/68* (2022.01)

(58) Field of Classification Search
CPC ... A01M 7/0089; A01M 7/0042; G06T 7/507; G06T 7/62; G06T 7/90; G06T 7/0006; G06T 2207/30188; G06V 20/188; G06V 20/68; B05B 1/20; B05B 12/122; G01N 33/0098
USPC .......................................................... 382/110
See application file for complete search history.

(56) References Cited

U.S. PATENT DOCUMENTS

| | | | | |
|---|---|---|---|---|
| 2012/0106097 | A1* | 5/2012 | Hsieh | G06F 1/3296 361/748 |
| 2018/0330166 | A1* | 11/2018 | Redden | A01M 7/0089 |
| 2019/0327919 | A1* | 10/2019 | Copeland | A01G 25/09 |
| 2020/0045953 | A1* | 2/2020 | Serrat | A01M 7/0089 |
| 2020/0073389 | A1* | 3/2020 | Flajolet | G06V 10/82 |
| 2021/0029892 | A1* | 2/2021 | Maehata | A01G 3/053 |

* cited by examiner

*Primary Examiner* — Michael R Neff
(74) *Attorney, Agent, or Firm* — Bay State IP, LLC

(57) ABSTRACT

It is a device designed to distinguish plants from agricultural soil (soil background); of the type that a photographic camera uses to proceed with the capture of images and process them in order to perform the detection of weeds, and from it, with the information obtained, to drive an actuator that controls the operation of corresponding media valves that command the work of the sprinklers arranged in the carrier boom of the sprayer, through which it is possible to apply herbicidal products, or exercise a control over them that may be mechanical or chemical.

4 Claims, 2 Drawing Sheets

DEVICE TO DETECT AND EXERCISE CONTROL OVER WEEDS APPLIED ON AGRICULTURAL MACHINERY

CROSS REFERENCE TO RELATED APPLICATION

This application takes priority from and claims the benefit of Argentina Patent Application Serial No. P 2019 0101488 filed on May 31, 2019, the contents of which are incorporated by reference.

BACKGROUND OF THE INVENTION

Field of the Invention

The present invention, for which the patent of the invention is sought, has as its main object a DEVICE TO DETECT AND EXERCISE CONTROL OVER WEEDS APPLIED ON AGRICULTURAL MACHINERY, such as a sprayer, from which it is possible to distinguish plants from the agricultural soil ("background" of soil), through the use of a high resolution digital photographic camera (Vga) associated with an integrated circuit such as a CCD sensor in specific bandwiths of the spectrum, to collect images that are processed identifying points of interest, and through them, to control an actuator that can, for example, apply herbicidal products, or to exercise a control over them that may be mechanical or chemical, taking into account the correction of the speed factor of the equipment.

More specifically, the invented device comprises an image capture element, a processor, and peripheral circuits associated with an actuator and corresponding wiring. It can be mounted on a sprayer to proceed with the capture of images and process them in order to perform the detection of weeds, and from there, with the information obtained, to drive an actuator that allows control over those weeds.

The invented device, using the aforementioned photographic camera (Vga) proceeds to take images in real time, and through the use of an algorithm for the detection of plant tissue, a second binary image is generated that differentiates plants from the rest of the image (soil, stubble).

With the invented device, from the detection of plants in the second image, taking into account the speed of advance, the distance to the sprayer tip that exercises the control and parameters of the image, a signal is instrumented that is sent to the actuator so that it can control the weeds detected in question, whether by means of spraying, mechanical, or other resources such as those that use chemicals.

It also includes a medium that, through an algorithm to detect failures will proceed to alert the user, and avoid application failures, either due to dirt on the camera lens, or the malfunction of any of the components.

Thus constituted, the invented device, for example, will be able to be arranged in the sprayer barrel of the agricultural implement, preferably in a position that lies ahead of it, taking into account the direction of progress of the implement.

This is an invention that defines a new combination of media designed to achieve a superior result, being the same unpredictable and surprising even for an expert in the field. Consequently, in addition to being new, its constructive and functional conception shows a clear inventive activity, so that it meets the conditions required by the Law to be considered an invention patent.

DESCRIPTION OF THE RELATED ART

The prior art shows various devices designed for a purpose similar to that carried out by the device to detect and control weeds of this invention, of which the following documentation stands out.

U.S. Pat. No. 5,768,823/1998

It refers to an application controlled with chemicals for weed control from a mobile sprayer. It discloses a specific method of selective application that uses detectors that identify weeds in a field of view and releases the application of individual nozzles. The moment of release of the herbicide from each nozzle is controlled in correspondence with the current speed of each nozzle. This speed is extrapolated from direct speed measurements taken from two separate places in the applicator apparatus, and the location of each individual nozzle in it.

U.S. Pat. No. 5,789,741/1998

It shows an Agricultural Implement created to detect plants in a field through the detection of a change in reflectance characteristics.

It discloses an implement such as a sprayer that differentiates living plants growing in a field, detecting a change in their reflectance. Using this change, a small percentage of living plant material in the field can be detected and the possible presence of a weed in the field of vision is determined. A solenoid valve opens at the appropriate time to spray the entire area (including the weeds) with herbicide.

U.S. Pat. No. 5,144,767/1992

This patent refers to a Controller for agricultural sprayers and shows an apparatus having a sensor (15) to determine irradiation in the red and infrared wave bands close to the electromagnetic spectrum and a plurality of sensors (13) to determine the irradiation of a target area to be sprayed on the closest red and infrared wave bands.

The controller commands the operation of individual sprinklers (12) by comparing the measurements taken by the sensors (15 and 13) and compares the relationship of these values (reflectance) to determine whether the sprayer for the target area in particular must be on or off. The determination can be made simply by looking up tables of reflectance values, or by calculating algorithms of nonlinear decision.

U.S. Pat. No. 5,507,115/1996

This patent discloses a system of selective application for weed control, using weed detectors that process four bandwiths of reflected illumination in a field of vision that may contain weeds. The same includes detectors distributed to control individual sprayer tips.

U.S. Pat. No. 9,030,549/2015

This patent discloses a method for an automatic plant necrosis. This is a method to distinguish individuals within a furrow of plants, including to direct radiation to the furrow at a selected angle, to illuminate a portion of the plant, and mark a shadow in the center of it. With this method we proceed to collect an image of the radiation reflected by two or more plants with a detector, identifying a continuous region that means plant within the image, identifying points of interest within that region, classifying them as centers of plant and non-centers of plant, and segmenting the region into subregions each around a point of interest classified as a center.

Analyzing the Descriptive Memory, we see that it is a system to thin out plants, taking as a novelty, in that it can distinguish "double strokes" as grouped plants, and not as an individual plant. It is also said that it can be used for weeds, or any other plant. It discloses a specialty of the method to be able to separate plants that are bound together by changing lights and shadows.

U.S. Pat. No. 9,064,173/2015

It is a patent very similar to the previous one that also refers to a method and a device for an automatic plant necrosis.

It shows a method to select in real time and remove from a field of plants including the capturing of a first image of a section of the field, segmenting this first image into regions indicative of individual plants within this section, selecting the optimal plants to retain from the first image based on it and the previous plant thinning information, sending instructions to the plant removal mechanism corresponding to the regions not selected, and repeating the process in successive images.

U.S. Pat. No. 9,717,171/2017

It refers to a method and system for a calibration of automatic odometry in precision farming systems.

The method explains the obtaining of a first image of a first region of the field, automatically, treating an "in situ" plant based on the image, automatically verifying the treatment with a second image of this first region, and automatically continue the scheme in successive images. It is a method to correct errors in the distance of the wheel used to measure distance, by processing the images to visually estimate the distance traveled.

U.S. Pat. No. 9,658,201/2017

It shows a method for automatic phenotyping measurement and plant selection. It discloses a system to detect plant parameters, including a morphology sensor having a first field of vision and configured to record a morphology measurement of a portion of the plant and the environment adjacent to it, a physiology sensor with a second field of vision and configured to record physiological parameters of a portion of the plant and the adjacent environment where this second field of vision overlaps the first.

A support that holds the sensors in a fixed way, and a computerized system configured to identify a set of plant pixels within the physiological measurement, based on the morphological measurement, determines physiological values for each pixel of this set and extracts growth parameters based on the physiology values.

U.S. Pat. No. 8,027,770/2011

It refers to a system for selective treatment of plants in a furrow extended in one direction that includes a camera arranged in the direction of the furrow over it, and a set of treatment units arranged at a fixed distance of the camera. The camera is configured to move through the direction of the furrows obtaining images of the area that includes one or more plants to be treated.

The set of treatment units is configured to move in the same way behind the camera keeping that fixed distance. The system generates a digital map of spots covering the area based on the images and sends the map to the computer unit where a treatment application adds specific treatment instructions to the generated map.

The system synchronizes the treatment units to treat each of the spots according to the application instructions.

In this case the novelty lies in using multiple small nozzles to distribute the application exactly over the plant.

U.S. Pat. No. 5,793,035/1996

It refers to an apparatus and method for spraying herbicides into weeds in a cotton field. Weeds that grow around the bases of the cotton plant stalks and are distributed in a row in a cotton field, are sprayed with herbicide without spraying the cotton stalks or wasting the herbicide on the ground.

Cotton plants are mature enough and their stalks exhibit a spectral reflectance characteristic significantly different from that of the weeds that typically grow in the middle of cotton.

Cotton plants are tall enough that most of the leaves of cotton plants are arranged outside the area that can be sprayed using an electronically controlled valve and nozzle.

Light is transmitted toward an object (a cotton stalk, a weed, or the ground) in the row and the reflected light is analyzed. If the object has a spectral characteristic of a growing weed, then the valve is activated, and the object is sprayed with herbicide.

U.S. Pat. No. 7,570,783/2009

It refers to a method and system for vehicular guidance using crop images.

The method and system comprise an image device for collecting color image data to distinguish crop image data (e.g., crop rows) from background data.

A definer defines a series of scan line segments generally perpendicular to a transverse axis of the vehicle or the imaging device.

An evaluator of image parameters determines the data of the scan line image parameters for each of the scan line segments.

An alignment detector (for example, a search engine) identifies a preferential direction of the vehicle that is generally aligned with respect to a crop characteristic, associated with the crop image data, depending on whether the image parameter of the determined scan line meets or exceeds a maximum or minimum threshold value.

A reliability estimator estimates a reliable vehicle direction based on the fulfillment of a criterion for scanning line image parameter data associated with one or more crop rows.

U.S. Pat. No. 6,574,363/2003

It refers to a method for color detection in video images.

This is a method to identify pixels of a certain color in a video field YUV manipulates the color difference signals (RY, BY) corresponding to the definition axes (U, V) of a color space to maximize the video signal in a region of interest in space, and minimize the signal in all other regions.

In addition, the color difference signal corresponding to one axis can be rotated towards the other axis, or the entire color space can be rotated to carry the region of interest toward or near one of the axes. The gains and rotations of the signal can be carried out in the signal processing circuits (52) of a conventional color camera (50) so that only one comparator (90) is needed to detect the target color.

After the rotation and gain application, the color difference signal that defines the region of interest is compared with a threshold value to determine if a pixel is of the target color.

A video camera can be mounted on an agricultural sprayer to detect green weeds on the brown ground, identifying the green pixels in the captured image while the sprayer travels in the field. A spray material can be released on the weed once the weed is detected.

It can be seen that an analog camera is used with every analog circuit, not included. It uses RGB color transformed to YUV.

U.S. Pat. No. 5,661,817/1997

In this case is disclosed a conventional CCD camera without an IR blocking filter used to detect desired vegetation from undesired and other material. This detection technique is based on the fact that NIR radiation is perceived by the CCD in a predetermined bandwidth.

This provides signals of green and blue pixels of the camera that are approximately equal in interest to the intensity of the portion of NIR captured by the red pixels. A filter is placed between the camera and the white area to restrict the light perceived by the camera to a bandwidth (600-1400 nm) which allows to compare the NIR component of the blue or green pixels with the NIR plus red of the red pixel.

U.S. Pat. No. 5,621,460/1997

It also refers to an optical differentiation between plants and background using a simple CCD camera.

An optical system to detect vegetation with the use of a single image sensor, such as a camera with an attached charging device (CCD), is provided by optical elements that project separate images of red and near infrared (NIR) into the CCD camera. The camera can then supply representative output signals of the two images to a signal processing device that determines the nature of the vegetation that the original image provided.

Embodiments are described in which the image sensor uses unitary optical dividers to provide separate wide-angle images. In another version, a single lens and a group of mirrors provide a telescopic device of narrow angle. Another version includes two separate lenses, red and NIR filters, each adjacent to one of the lenses to project an image in separate areas of the CCD camera.

U.S. Pat. No. 5,606,821/1997

An intelligent system of recognition and identification composed of a chlorophyll sensor to detect green vegetation and a way to memorize and save images which contain different forms of vegetation is disclosed.

Those maps are processed to eliminate background information leaving only green vegetation. This enhanced map is processed by segmentation in identifiable regions and identifiable vegetation is processed to identify unique attributes for each region.

These attributes are stored in a reference database to compare by means of a processor that relates the vegetation to the database then allows to control a plurality of sprayer nozzles covering the censored area.

It should be noted that none of the aforementioned equipment and devices shows, or at least suggests how to use a high resolution digital camera (Vga) associated with a CCD integrated circuit from which the information is sent to the processor so that in addition to identifying green colors, it provides a crop identification parameter. In this way we can enter a terrain that contains a crop X with other green objects and that each "device" identifies in said crop X any object that complies with the conditions of being green and that does not correspond to the characteristics of crop X, be subjected to the action of a herbicide.

In summary the device to detect and exert control over weeds of this invention presents three determining aspects that have not been disclosed by any of the aforementioned antecedents, namely:

1. Use of a VGA camera that has an integrated CCD circuit that includes artificial intelligence that includes media so that, in addition to identifying green colors, it provides a parameter of identification.
2. Pattern recognition.
3. Image process and execution of an order in real-time at working speed*(working speed is understood as the speed at which the device moves in the sprayer, 10 to 14 km/h approximately).

SUMMARY OF THE INVENTION

The device for detecting and exercising control over weeds applied in agricultural machinery of this invention, carries out a process to distinguish plants from the soil, using a CCD sensor whose images are processed identifying points of interest to control an actuator through which it is possible to apply herbicides focused on them, taking into account the correction of the speed factor of the equipment.

Likewise, with the invented device it is possible to store all the information of the actuated useful for later analysis.

With the controller it will be possible to command valves, which are actuated from pulses to generate different application doses according to the parameters used.

For this, the invented device has been designed, for example, to be mounted on the front of a sprayer by proceeding with the capture of images, each of which is properly processed, and from this, depending on the parameters that are obtained, produce the actuation of an actuator that exercises control of the aforementioned sprayer valves.

With the referred high-definition camera and the CCVD sensor, proceed to the taking of a first image in real time and using an algorithm to detect plant tissue, which generates a second binary image. This second image differentiates plants from the rest of the image (soil, stubble). From the detection of plants in the second image, taking into account the forward speed, the distance to the sprayer tip that exercises the control, and the parameters of the image, a signal sent to the actuator is instrumented so that it exercises control over the detected weeds in question, either by means of spraying, or other mechanical processes.

The invented device also implements a communication method that allows real-time monitoring of operation, and data recording in a central unit formed by a multimedia electronic touch and wireless device with a connection module. The data collected incorporate the number of detections, percentage of the applied area, and other georeferenced to be able to be synthesized in a map of the work done by the team.

The invented device also incorporates a fault detection algorithm to alert the user, and avoid application failures, either due to dirt on the camera lens or to the malfunction of any component.

No device to distinguish plants from the soil of those known currently proposes, or even suggests the constructive solution that arises from what is indicated in the preceding paragraphs, which is why it is a proposal that, in addition to being innovative, has a clear inventive activity.

BRIEF DESCRIPTION OF THE DRAWINGS

To specify the advantages thus briefly commented, to which users and experts in the field can add many more, and to facilitate the understanding of the constructive, constitutive and functional features of the device invented to detect and exercise control over weeds, a preferred embodiment example is described below, which is illustrated, schematically and without a certain scale, in the attached sheets, with the express clarification that, precisely, because it is an example, it is not appropriate to assign to it a limiting or exclusive character of the scope of protection of the present invention, but it simply assists as a purely explanatory and illustrative intention of the basic conception on which it is based.

DETAILED DESCRIPTION OF THE SEVERAL EMBODIMENTS

Figure 1:
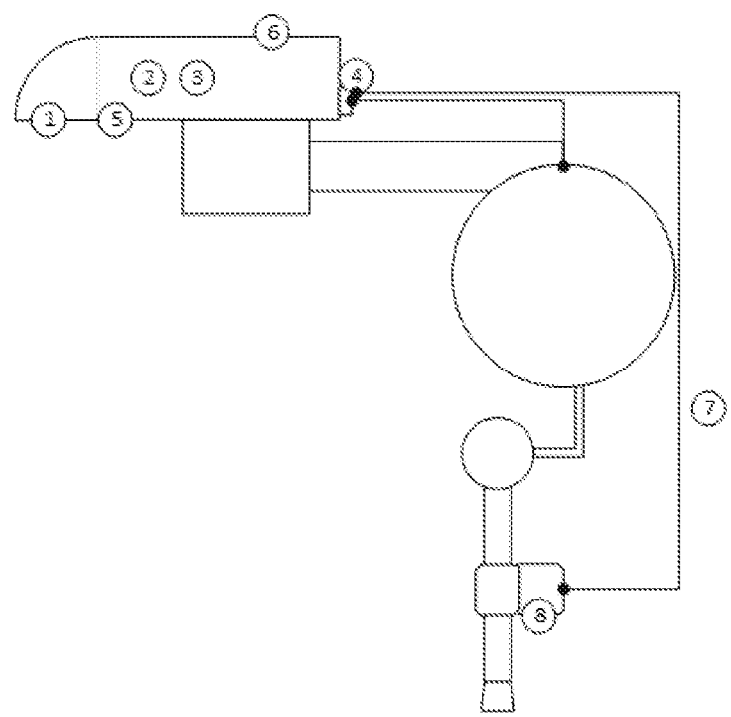
FIG. 1 is a schematic side view representing the basic elements that integrate the device of this invention.

As it is schematically represented in the first two figures, the device to detect and exercise control over weeds applied in agricultural machinery referred to in the present invention is formed on the following basic elements:

A cabinet (6) in which are housed the components that are arranged in the front of the sprayer boom.

An image capture device, in this case a Vga camera (1) associated with a CCD integrated circuit.

A processor (2), which evaluates the images supplied by the camera (1).

A plate (3), which is the link between the control console that is housed inside the cabin and also transmits the order to open to the solenoid valve (8).

Waterproof connectors (4), through which information and data transmission is channeled.

Solenoid valve (8), a component that is arranged on the tip carrier of the sprayer bar, it is responsible for allowing or not the passage of the spray fluid.

With the reference (7) of FIG. 1, the cable for transmitting communication (cabinet/valve) is shown.

Wiring (11), responsible for supplying energy necessary for the device to fulfill its function and transmit information to the cabin and vice versa.

Figure 2:
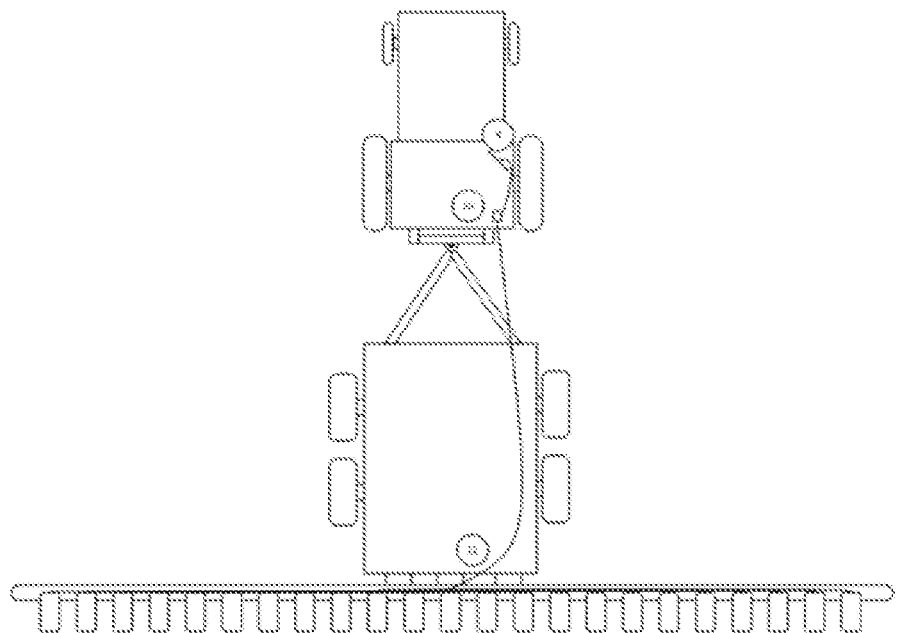
FIG. 2 is a top plan view showing an agricultural spraying device that has the device of this invention installed.

The presence of the monitor inside the cabin is indicated in FIG. 2 with reference (9).

In the same FIG. 2 with reference (10) the protocol translator is represented, in charge of coding the signal that comes from the boom to a language suitable for the internal console, through which the operation of each device is shown allowing parameters to be modified.

Thus, the invented device is constituted, as schematically represented in FIG. 2, it is arranged mounted on the sprayer boom, at the rate of one device per sprayer tip, in a position preceding the boom, taking into account the direction of advance.

When a green colored object is captured, the order to open is given to the solenoid valve, thus carrying out the application of the herbicidal product on said object, with the particularity that when using a high definition Vga camera associated with a CCD integrated circuit, in addition to identifying green colorations it provides other crop identification parameters so that it can identify other green objects that do not correspond to the characteristics of the crop, on which it is necessary to apply the herbicidal fluid.

In case a green object is not detected, the application will not be performed.

Based on the known, the aforementioned possibility that, in addition to identifying green colors, a crop identification parameter is provided, which specifically distinguishes it from weeds, confers on this device greater precision and functional efficiency. For this, an algorithm to detect plant tissue is used, which generates a second binary image. This second image differentiates plants from the rest of the image (soil, stubble). It is about setting up a series of decision-making rules using artificial intelligence tools to differentiate crops from weeds and the type of weeds.

Figure 3:
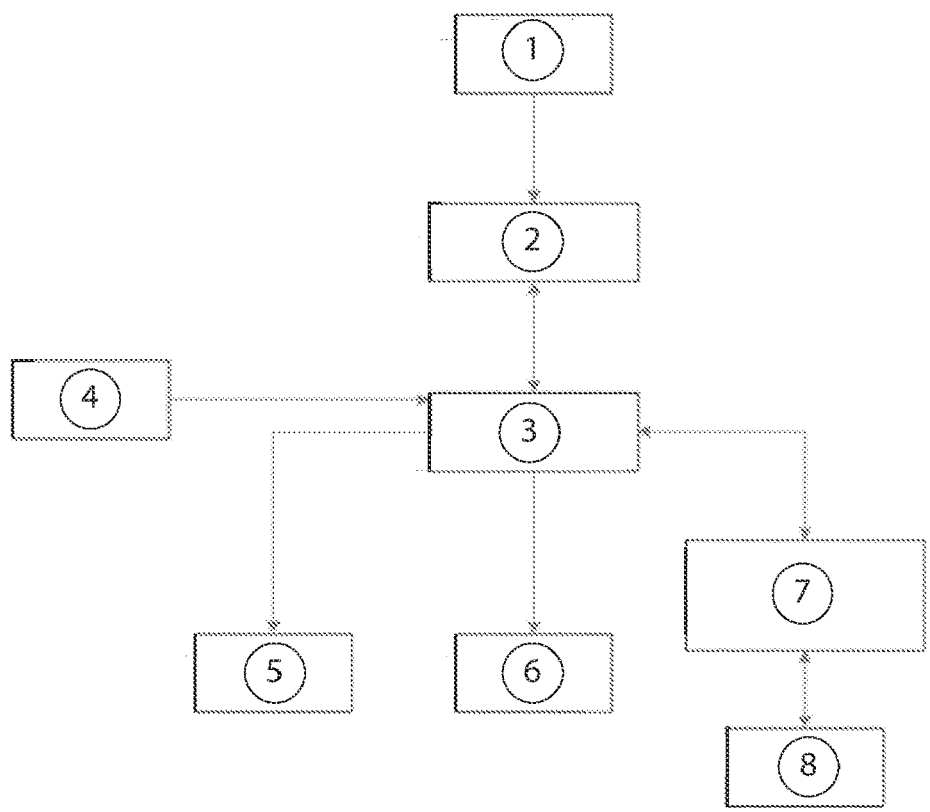
FIG. 3 is a block diagram that explains how the invented device works.

Now observing the block diagram of FIG. 3, it is schematically appreciated the operating principle of the device of this invention, putting into practice the following operational succession:

1. The capture of image of the surface on which the spraying machine advances is produced.
2. The image being captured is processed.
3. The processed information is transferred.
4. Electric power is provided.
5. A lighting source is included.
6. With the processed information (3) the valve opening occurs.
7. With the processed information (3) the communication protocol is established.
8. Information monitoring is also established.

As the aforementioned diagram in FIG. 3 shows, the process begins with the capture of images in real time by means of a Vga camera (1).

These images are evaluated by the processor (2), which by means of an algorithm differentiates plant material from other objects.

The results obtained from the analysis are transmitted by means of the plate (3) to the different destinations. One of them is the solenoid electric valve (normally closed) (indicated with reference (8) in FIG. 1), which, depending on the image processing result, will enable the corresponding nozzle to spray on the green plant material that is in line with the camera.

The other destination is the protocol translator (see block 7) which is responsible for encoding the signal from the cabinets (6) arranged on the boom, to a language suitable for the internal console through which it is possible to see the operating status of the different devices, it also allows to correct and adjust the camera's viewing angle.

On the other hand, block 5 represents a circuit to power an LED for lighting (5) of the target. The power supply that represents block 4, is directly connected to the cabinets which provide the necessary electricity for all the LEDs (5), plate (3), camera processor (2) and solenoid valve (8).

Figure 4:
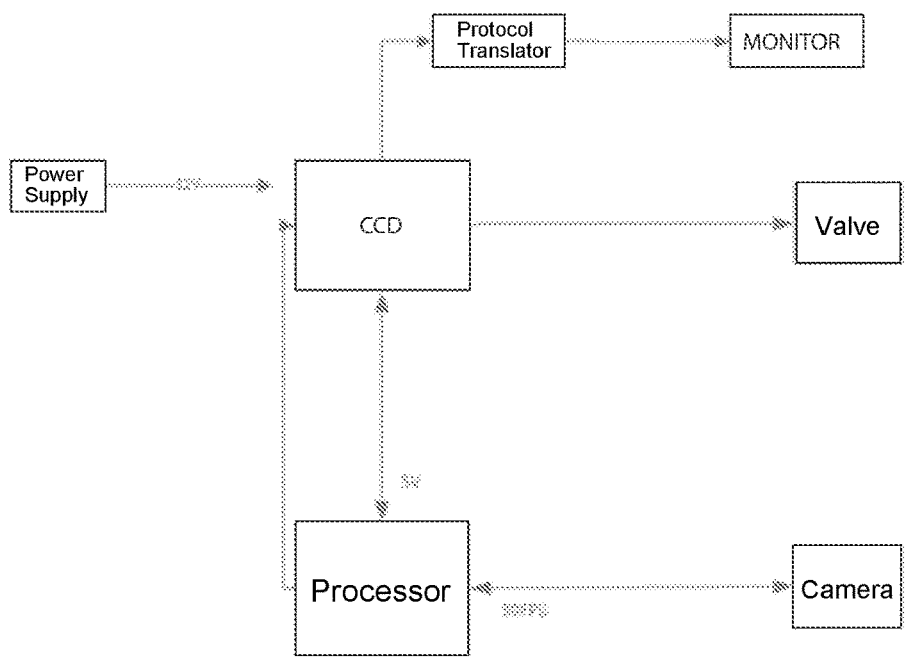
FIG. 4 is also a block diagram showing the internal operation of the invented device.

Now observing FIG. 4, it is possible to appreciate the internal operation of the invented device.

The 12v power supply is transformed by the CCD to 5v which are necessary to send the work order to the processor, the camera, and the valve.

The processor sends a work order to the camera to begin the process of taking pictures at 30 fps from the surface.

The captures are analyzed and processed by a software in the processor. The results obtained are sent as a work order to the CCD. It transmits a signal with a certain frequency and bandwidth (according to the information received) to the valve. The variation in frequency and bandwidth of the signal can be achieved by being a PWM connection valve.

On the other hand, the Processor sends a report (summary style) by serial communication to the CCD. This translates it for a CAN communication and then sends it to the monitor. Prior step to receiving the information, there is a protocol translator that converts CAN communication to serial again so that the monitoring device can read it.

It is a device designed to distinguish plants from agricultural soil (soil background); of the type that a photographic camera uses to proceed with the capture of images and process them in order to perform the detection of weeds, and from it, with the information obtained, to drive an actuator that controls the operation of corresponding media valves that command the work of the sprinklers arranged in the carrier boom of the sprayer, through which it is possible to apply herbicidal products, or exercise a control over them that may be mechanical or chemical. It comprises a high resolution digital camera Vga (1), associated with a CCD integrated circuit, from which information is sent to a processor (2), which evaluates the images supplied by the digital camera through an algorithm that differentiates plant material from other objects and drives an electronic controller that acts as a link between the control console, which is housed inside the cabin, transmitting the order to each solenoid valve to open, arranged on the tip holder of the boom, which controls the operation of a respective spray tip; the device includes corresponding watertight connectors, through which information and data transmission are channeled; including a media protocol translator, responsible for coding the signal that comes from the boom to a language suitable for the internal console, through which the operation of each device is shown allowing parameters to be modified. A 12v power supply is transformed by the CCD to 5v which are necessary to send the work order to the processor, to the camera, and to each valve, it is directly connected to the cabinets arranged in correspondence of each valve on the boom, to provide the necessary electricity for both the LEDs (5), plate (3), camera processor (2) and solenoid valve (8). The processor sends a work order to the Vga camera so that it begins with the process of taking images at 30 fps from the surface, each of which is analyzed and processed by software, whose results are sent as a work order to the CCD that transmits a signal with a certain frequency and width (according to the information received) to each valve. Also, through serial communication to the CCD, who translates it for CAN communication and then sends it to the monitor; prior step to receiving the information, a protocol translator is used that converts CAN communication into serial again so that a monitoring device can read it. The protocol translator is responsible for coding the signal from the valve-carrying cabinets arranged on the boom, to a language suitable for the internal console through which it is possible to see the operating status of the different devices, correct and regulate the viewing angle of each camera.

What is claimed is:

1. A device to detect and exercise control over weeds applied in agricultural machinery designed to distinguish plants from agricultural soil (soil background) with a camera to proceed with the capture of images and process the images in order to perform detection of weeds, and with information obtained from the detection processing of the images, to drive an actuator that controls the operation of corresponding media valves that command the work of sprinklers arranged in a carrier boom of a sprayer, through the actuator it is possible to apply herbicidal products, or exercise a control over the actuator that can be mechanical or chemical, wherein the device comprises:

a digital camera (Vga)(1), associated with a charge-coupled device (CCD) integrated circuit, from which information is sent to a processor (2), which evaluates the images supplied by the digital camera through an algorithm that through decision-making rules defined with artificial intelligence tools train an equipment in the differentiation of plant material from other objects, and the processor activates an electronic controller that acts as a link between a control console, which is housed inside a cabin, transmitting an order to each solenoid valve to open, arranged on a tip holder part of the boom, which commands the operation of a respective sprayer tip; the device includes corresponding watertight connectors, through which information and data transmission are channeled; including a media protocol translator, responsible for coding a signal that comes from the boom to a language suitable for the control console, through which the operation of each device is shown allowing parameters to be modified;

wherein a 12v power supply is transformed by the CCD to 5v that are necessary to send a work order to the processor, the digital camera, and to each valve; and wherein the power supply is directly connected to a cabinets arranged in correspondence to each valve on the boom, to provide the necessary electricity for each of a LED (5), a plate (3), a camera processor (2) and a solenoid valve (8).

2. The device to detect and exercise control over weeds applied in agricultural machinery, as claimed in claim 1, characterized in that the processor sends a work order to the digital camera to begin a process of taking images at 30 fps from a surface, each of which is analyzed and processed by a software, whose results are sent as a work order to the CCD that transmits a signal with a determined frequency and width to each valve.

3. The device to detect and exercise control over weeds applied in agricultural machinery, as claimed in claim 1, characterized in that the processor sends a report via serial communication to the CCD, the CCD translates the report for a Controller Area Network (CAN) communication and then sends the report to a protocol translator; the protocol translator converts the report from a CAN communication into serial again, and sends the report to be read by a monitoring device.

4. The device to detect and exercise control over weeds applied in agricultural machinery, as claimed in claim 3, characterized in that the protocol translator is responsible for encoding the signal from the cabinets arranged on the boom, to a language suitable for the control console; and through the control console seeing an operating status of different devices, as well as correcting and regulating a viewing angle of each camera.

* * * * *